(12) United States Patent
Whitehead et al.

(10) Patent No.: US 11,510,906 B1
(45) Date of Patent: *Nov. 29, 2022

(54) DIAZACYCLOBUTENE DERIVATIVES AS ANTI-PARASITIC DRUG SUBSTANCES

(71) Applicant: Clemson University, Clemson, SC (US)

(72) Inventors: Daniel C. Whitehead, Clemson, SC (US); James C. Morris, Clemson, SC (US); Chandima J. Narangoda, Clemson, SC (US)

(73) Assignee: Clemson University, Clemson, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/811,135

(22) Filed: Mar. 6, 2020

Related U.S. Application Data

(60) Provisional application No. 62/817,119, filed on Mar. 12, 2019.

(51) Int. Cl.
*A61K 31/4196* (2006.01)
*A61P 33/02* (2006.01)
*A61K 31/502* (2006.01)

(52) U.S. Cl.
CPC ........ *A61K 31/4196* (2013.01); *A61K 31/502* (2013.01); *A61P 33/02* (2018.01)

(58) Field of Classification Search
CPC .... A61K 31/502; A61K 31/4196; A61P 33/02
See application file for complete search history.

(56) References Cited

PUBLICATIONS

Narangoda et. al. (Org. Lett. (2018) 20:8009-8013). (Year: 2018).*
Ito et. al. (Cancer Science (2003) 94:3-8). (Year: 2003).*
Narangoda et al., Accessing the Rare Diazacyclobutene Motif, 2018, Organic Letters, 20, 8009-8013 (Year: 2018).

* cited by examiner

*Primary Examiner* — Marcos L Sznaidman
(74) *Attorney, Agent, or Firm* — Joseph T. Guy; Patent Filing Specialist Inc.

(57) ABSTRACT

A drug product and method for treating a parasitic disease in a host is described. The drug product comprises:
a carrier matrix; and
a drug substance having the formula:

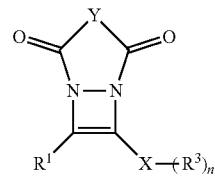

wherein:
$R^1$ is selected from the group consisting of H, aliphatic of 1 to 100 carbons and arene comprising up to 100 carbons;
each $R^3$ is independently selected from the group consisting of H, aliphatic of 1 to 100 carbons and arene comprising up to 100 carbons;
Y represents those elements necessary to form a 5 or 6 membered ring;
X is selected from the group consisting of B, O, N, S, Se and P; and
n is 1-4 as necessary to complete the valence of X.

21 Claims, 3 Drawing Sheets

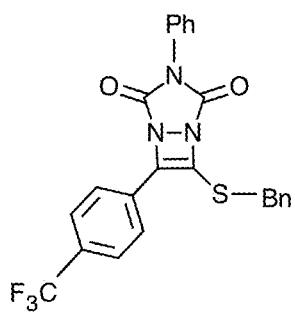 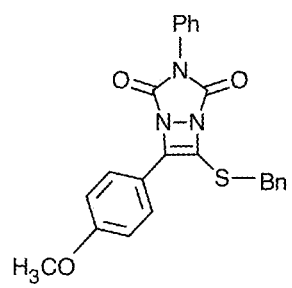 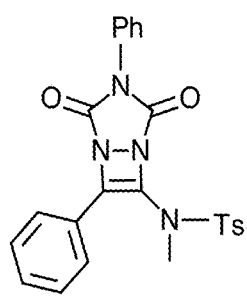
Compound 19   Compound 20   Compound 21
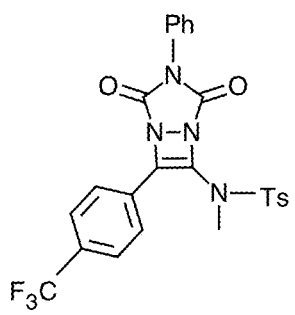 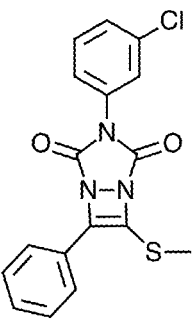 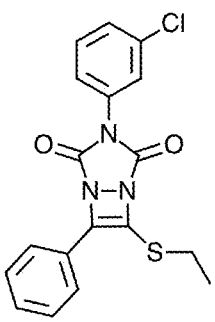 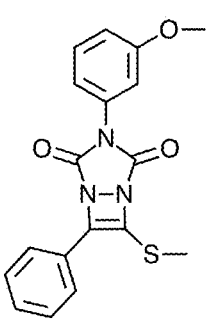
Compound 22   Compound 23   Compound 24   Compound 25
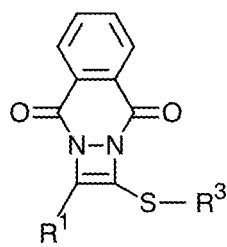 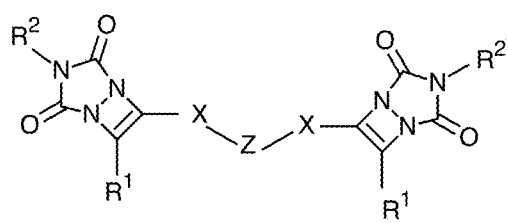
Compound 26   Compound 27
FIG. 1B
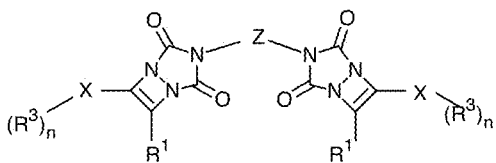
Compound 28

DIAZACYCLOBUTENE DERIVATIVES AS ANTI-PARASITIC DRUG SUBSTANCES

CROSS-REFERENCE TO RELATED APPLICATIONS

This application claims priority to U.S. Provisional Application No. 62/817,119 filed Mar. 12, 2019 which is incorporated herein by reference.

FIELD OF THE INVENTION

The present invention is related to diazacyclobutene derivatives as anti-parasitic compounds and particularly for treatment of kinetoplastid parasites, particularly parasites responsible for Human African Trypanosomiasis (HAT), Chagas disease, and leishmanaisis. Particularly suitable diazacyclobutene derivatives are compounds of Formula I:

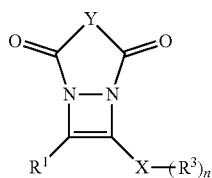

Formula I with a particularly preferred embodiment represented by Formula II:

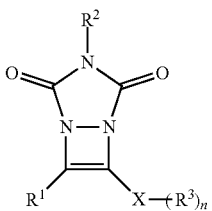

Formula II which are described herein along with the synthesis thereof wherein $R^1$, $R^2$, $R^3$, Y, X and n are defined further herein.

BACKGROUND

*Trypanosoma brucei* gambiense (chronic HAT) and *Trypanosoma brucei* rhodesiense (acute HAT) are parasitic diseases carried by tsetse flies. The disease is most prevalent, but not limited to, South Africa, the Democratic Republic of the Congo and surrounding regions. Related diseases, Chagas disease and leishmaniasis, caused by *Trypanosoma cruzi* and *Leishmania* spp., are more prevalent in North and South America, Southeast Asia, and parts of Europe and Australia.

The life cycle of chronic HAT and acute HAT, specifically, are propagated through the interaction of a host, particularly humans, and the tsetse fly. The tsetse fly, upon taking a blood meal from the host, injects metacyclic trypomastigotes into the blood stream of the host wherein it is transported to other sites within the host, specifically to other body fluids or tissues. The injected parasites differentiate into long slender forms in the body fluids, wherein they multiply by binary fission. Long slender parasites, upon detecting a quorum-dependent cue, differentiate into non-dividing short stumpy parasites. Upon a subsequent blood meal by a tsetse fly the short stumpy parasites from the blood stream of the host are ingested by the tsetse fly wherein they transform in the midgut of the tsetse fly to procyclic form. The procyclic form parasites leave the midgut of the tsetse fly and transform into epimastigotes in the salivary gland and ultimately differentiate into metacyclic trypomastigotes in the salivary glands which are available for injection upon the next blood meal by the tsetse fly.

Chronic HAT, also referred to as West African HAT, and Acute HAT, also referred to as East African HAT, are debilitating diseases. Both exhibit a hemolymphatic stage wherein the parasites invade the blood and lymph resulting in symptoms such as intermittent fever, malaise, headache, itching and swelling of the lymph nodes. If untreated, the hemolymphatic stage is followed by a meningoencephalitic stage wherein the parasites invade the central nervous system. The symptoms of the meningoencephalitic stage include severe headaches, sleep irregularity, tremors, limb paralysis, psychiatric symptoms, coma and death. Chronic HAT typically progresses over a longer period, such as about three years, whereas acute HAT progresses rapidly such as in several weeks or months.

The occurrence of HAT has been mitigated by vector control in past decades yet the diseases have seen a recurrence in the last few decades due to various socio-economic issues around the world. Various agencies across the globe, such as the World Health Organization, have estimated that large numbers of the population are either infected by, or vulnerable to, one form of the disease or the other.

Treatments have been provided in the past. Suramin and pentamidine, both of which are primarily stage 1 drugs suitable for use in the hemolymphatic stage, are marginally effective. Melarsoprol, eflornithine, nifurtimox-eflornithine and fexinindazole are either on the market or in clinical trials as stage 2 drugs suitable for use in the meningoencephalatic stage. Though helpful, the currently available drugs are not sufficient for mitigating the disease.

Diazacyclobutenes are a unique class of four membered heterocycles consisting of a carbon-carbon double bond and two adjacent nitrogen atoms. Diazacyclobutenes have long been sought for their expected utility in synthesis and for exploration of their reactivity. The availability of diazacyclobutenes has been limited by their difficult synthetic path and therefore only a few have been available for study.

Through diligent research a novel synthetic approach has been developed which makes a large class of diazacyclobutenes available for further research into their viability as synthetic tools and of their potential reactivity and functionality in a variety of systems. Newly available diazacyclobutenes which are effective against various parasites, particularly, those recognized as the culprit in various forms of HAT and related parasite-borne diseases, and treatment based thereon, are provided herein.

SUMMARY OF THE INVENTION

The invention is related to novel anti-parasitic compounds and their use.

More specifically, the present invention is related to treatment against parasites based on newly available diazacyclobutenes as a drug substance.

These and other embodiments, as will be realized, are provided in a drug product comprising a carrier matrix and a drug substance. The drug substance has the formula:

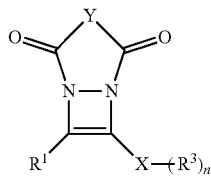

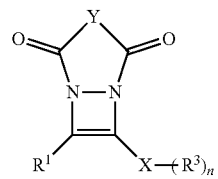

Formula I wherein:
R¹ is selected from the group consisting of H, aliphatic of 1 to 100 carbons and arene comprising up to 100 carbons;
each R³ is independently selected from the group consisting of H, aliphatic of 1 to 100 carbons and arene comprising up to 100 carbons;
Y represents those elements necessary to form a 5 or 6 membered ring;
X is selected from the group consisting of B, O, N, S, Se and P; and
n is 1~4 as necessary to complete the valence of X.

Yet another embodiment is provided in a method of treating a parasitic disease in a host comprising the steps of: providing a drug product comprising:
a carrier matrix; and
a drug substance having the formula:

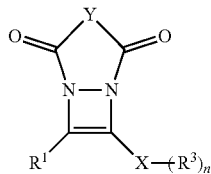

wherein:
R¹ is selected from the group consisting of H, aliphatic of 1 to 100 carbons and arene comprising up to 100 carbons;
each R³ is independently selected from the group consisting of H, aliphatic of 1 to 100 carbons and arene comprising up to 100 carbons;
Y represents those elements necessary to form a 5 or 6 membered ring;
X is selected from the group consisting of B, O, N, S, Se and P; and
n is 1~4 as necessary to complete the valence of X; and
administering an effective dose of drug product to the host.

BRIEF DESCRIPTION OF FIGURES

FIGS. 1A and 1B comprises schematic structures of various embodiments of the drug substance of the invention.

DESCRIPTION

Figure 1A:
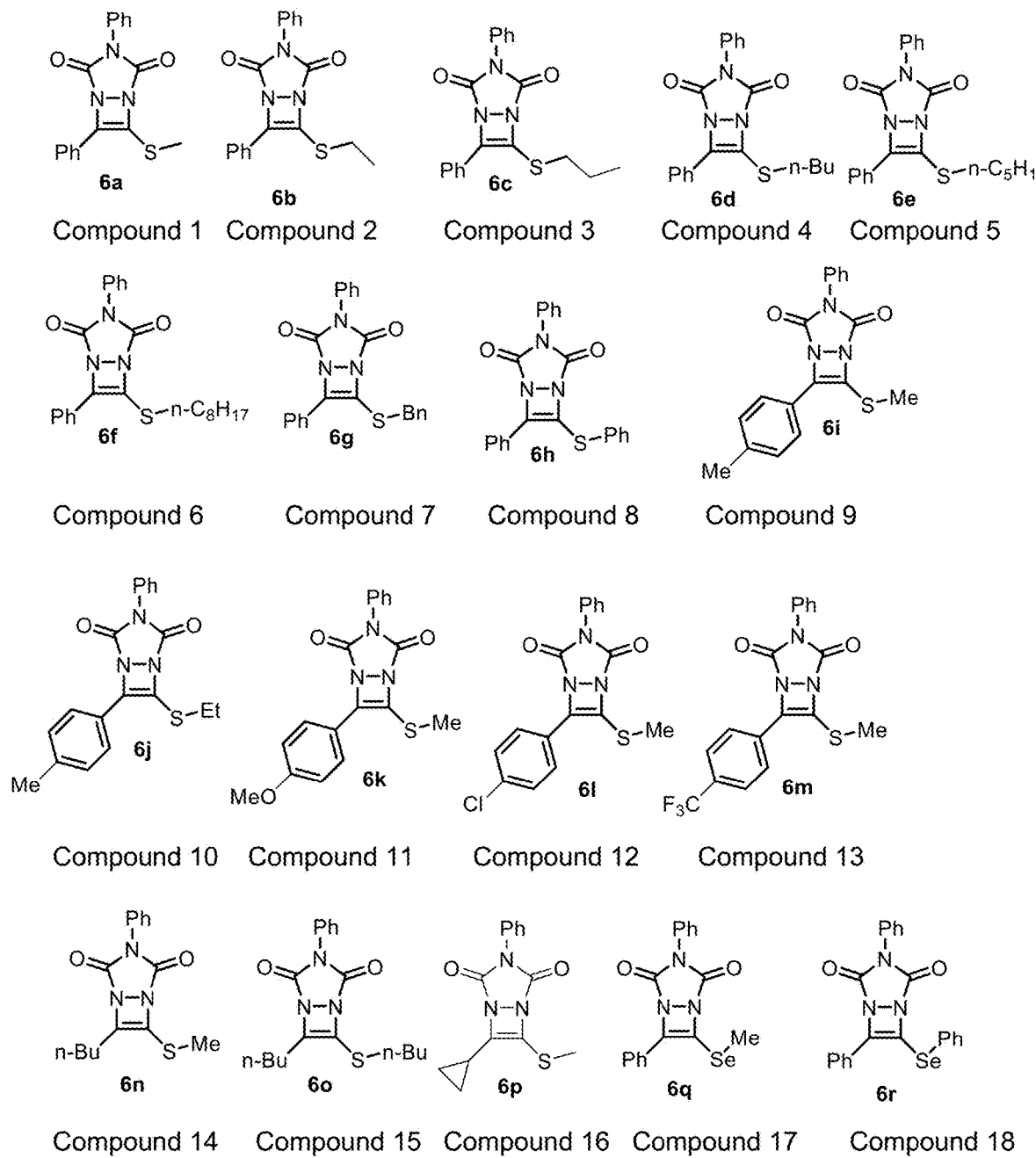

The present invention is related to a method of treating parasite propagated diseases. More specifically, the present invention is related to the treatment of various diseases, particularly kinetoplastid infections and related diseases by drug products comprising diazacyclobutene derivatives as a novel drug substance.
Diazacyclobutene derivatives are compounds of Formula I:

which are described herein, along with the synthesis thereof, wherein R¹, R³, Y, X and n are defined further herein and described herein as being suitable for the treatment of infections resulting from kinetoplasid parasites such as *Trypanosoma brucei* gambiense (chronic HAT), *Trypanosoma brucei* rhodesiense (acute HAT), *Trypanosoma cruzi* (Chagas disease) and *Leishmania* spp. (leishmanaisis), without limit thereto, all of which are parasitic diseases carried by insect vectors.

The compound of Formula I as a drug substance is preferably administered to a host in a suitable carrier to form a drug product. The carrier can be a solid, liquid or an aerosol. The method of administration is not particularly limited herein with suitable delivery methods including oral dosage, sublingual doses, injectable doses, inhalation doses, absorption through mucosal membranes and combinations thereof. Suitable mucosal membranes for administration include ocular, nasal, pulmonary, buccal, sublingual, gingival, rectal, and vaginal mucosal membranes. Injectable dosages can be by intravenous injection, intradermal, intramuscular, or subcutaneous. Oral dosage may be absorbed in the low pH region of the stomach or in the relatively higher pH region of the intestine.

The amount of drug substance administered initially in an effective dose is dependent on many factors including the advancement of the disease, the health and weight of the patient and related factors. In clinical use, it is preferable to administer an effective dose with an initial amount of drug substance based on clinical evaluation followed by at least one subsequent effective dose with a drug substance amount dependent on the plasma concentration after a pre-determined time such as 72 hours. Though not limited herein the effective dose, in most patients, is expected to range from about at least 0.5 mg to about no more than 1000 mg of drug substance per administration per host kg with subsequent doses being adjusted, preferably within the same range, based on plasma levels at a predetermined time. In some cases, multiple doses may be administered to the host over a period of time such as daily, weekly, monthly or longer depending on the plasma level and metabolism rate of the drug substance.

The synthesis of the diazacyclobutanes is accomplished by means of a formal [2+2] cycloaddition between, preferably, alkynyl sulfides or selenides and a compound of Formula I with 4-phenyl-1,2,4-triazoline-3,5-dione (PTAD) being exemplary for demonstration of the invention. This effort provides ready access to a molecular scaffold that was hitherto inaccessible, with the exception of a handful of examples.

Diazacyclobutene derivatives can be prepared by the reaction of selected compounds of the formula:

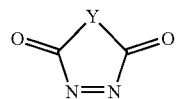

with the reaction being described using, as an exemplary embodiment, 1,2,4-triazoline-3,5-diones of Formula III:

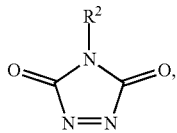

Formula III with alkynyl species of Formula IV:

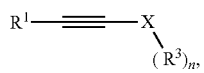

Formula IV wherein $R^1$, $R^2$, $R^3$, Y, n and X are described elsewhere herein, to form a derivative of diazacyclobutene of Formula I represented for the purposes of discussion by the exemplary embodiment thereof as Formula II without limit thereto. Exemplary compounds of Formula I:

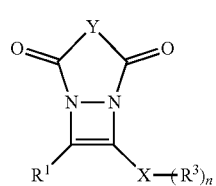

Formula I are illustrated schematically in FIGS. 1A and 1B without limit thereto.

The reaction of the compound of exemplary Formula III and the compound of Formula IV is preferably done in dry glassware, such as flame dried. The compound of Formula III and the compound of Formula IV are added and allowed to react, preferably at or above a reaction temperature and more preferably at reflux temperature of the solvent for a sufficient time to allow for complete reaction. The reaction temperature is preferably at least −20° C. to no more than 300° C. A temperature of 50° C. to 250° C. is suitable for demonstration of the invention with about 100° C. to 200° C. being preferred. The reaction time required is dependent on temperature with at least about 6 hours to no more than about 24 hours being preferred. Below about 6 hours yields can be compromised and above about 24 hours is unnecessary in most embodiments. The reaction product is obtained by removing solvent, preferably under reduced pressure, with purification. While not limited thereto, flash chromatography is a particularly suitable purification method for demonstration of the invention. Flash chromatography accomplished with hexane and ethyl acetate in a gradient from 100% hexane to 80:20 hexane/ethyl acetate is suitable for demonstration of the invention. It is preferable that the compound of Formula III be dissolved in a suitable solvent with dropwise addition of the compound of Formula IV in a solvent, and preferably the same solvent as Formula III, for convenience. In an alternate embodiment catalyzing the reaction of Formula III and Formula IV with a Lewis Acid catalyst, such as, but not limited to, silver (I) triflate is advantageous. The Lewis Acid catalyst is particularly preferred when X is a nitrogen.

In the formulas, $R^1$ and $R^2$ are independently selected from the group consisting of H, aliphatic of 1 to 100 carbons and arene comprising up to 100 carbons or combinations thereof. The aliphatic or arene may be unsubstituted or substituted with a substituent selected from the group consisting of halogen, aliphatic, arene, hydroxyl, carboxyl, carbonate, ester, acetal, acid halide, thioester, aldehyde, ether, carbamate, amine, amide, nitro, imine, urea, oxime, hydrazine, azo, azide, isocyanate, ketene, nitrone, nitroso, nitrate ester, acyl, thiol, thioacetal, sulfide, disulfide, sulfoxide, sulfone, sulfonic acid, thiosulfonate, sulfonate ester, sulfate ester, thiocyanate, phosphine oxide, phosphite ester, phosphonate ester, phosphate ester, phosphate, phosphine, phosphite, borane, boric acid, boronic acid, borate ester, acyl halide, acyl anhydride, nitrile or an organometallic. $R^1$ or $R^2$ independently are preferably selected from the group consisting of aliphatic of 1-10 carbons more preferably 1-5 carbons, arene of up to 20 carbons more preferably no more than 6 carbons, substituted aliphatic of 1-10 carbons more preferably 1-5 carbons or substituted arene of up to 20 carbons and more preferably no more than 6 carbons. The preferred substituents are selected from the group consisting of halogen, hydroxyl, carboxyl, and amine. Preferably at least one of $R^1$ or $R^2$ comprises a phenyl group.

In the formulas, X is selected from the group consisting of B, O, N, S, Se and P with S and Se, being preferred.

In the formulas, n is 1-4 as necessary to complete the valence of X. When n is more than 1 each $R^3$ can be the same or defined independently. It is preferred that n is 1 or 2.

In the formula, Y represents those elements necessary to form a 5 or 6 member ring preferably selected from the group consisting of C, N, O and combinations thereof wherein Y may be substituted. Particularly preferred are —$(CR^4_A)_m$—, —$NR^2$— or —O— wherein m is an integer selected from 1 and 2, A is an integer of 1 or 2, $R^2$ is defined elsewhere herein and each $R^4$ is independently selected from the group consisting of H, aliphatic of 1 to 100 carbons and arene comprising up to 100 carbons or combinations thereof. The aliphatic or arene may be unsubstituted or substituted with a substituent selected from the group consisting of halogen, aliphatic, arene, hydroxyl, carboxyl, carbonate, ester, acetal, acid halide, thioester, aldehyde, ether, carbamate, amine, amide, nitro, imine, urea, oxime, hydrazine, azo, azide, isocyanate, ketene, nitrone, nitroso, nitrate ester, acyl, thiol, thioacetal, sulfide, disulfide, sulfoxide, sulfone, sulfonic acid, thiosulfonate, sulfonate ester, sulfate ester, thiocyanate, phosphine oxide, phosphite ester, phosphonate ester, phosphate ester, phosphate, phosphine, phosphite, borane, boric acid, boronic acid, borate ester, acyl halide, acyl anhydride, nitrile or an organometallic. When m is 2, independent $R^4$ groups may be taken together to form an organic ring, a heteroatom ring or an arene. In a particularly preferred embodiment m is 2 and independent $R^4$ groups are taken together to form a phenyl ring.

In the formulas, $R^3$ is independently selected from the group consisting of H, aliphatic of 1 to 100 carbons and arene comprising up to 100 carbons or combinations thereof. The aliphatic or arene may be unsubstituted or substituted with a substituent selected from the group consisting of halogen, aliphatic, arene, hydroxyl, carboxyl, carbonate, ester, acetal, acid halide, thioester, aldehyde, ether, carbamate, amine, amide, nitro, imine, urea, oxime, hydrazine, azo, azide, isocyanate, ketene, nitrone, nitroso, nitrate ester, acyl, thiol, thioacetal, sulfide, disulfide, sulfoxide, sulfone, sulfonic acid, thiosulfonate, sulfonate ester, sulfate ester, thiocyanate, phosphine oxide, phosphite ester, phosphonate ester, phosphate ester, phosphate, phosphine, phosphite, borane, boric acid, boronic acid, borate ester, acyl halide, acyl anhydride, nitrile or an organometallic. $R^3$ independently are preferably selected from the group consisting of aliphatic of 1-10 carbons more preferably 1-5 carbons, arene of up to 20 carbons more preferably no more than 6 carbons, substituted aliphatic of 1-10 carbons more preferably 1-5 carbons or substituted arene of up to 20 carbons and more preferably no more than 6 carbons. The preferred substituents are selected from the group consisting of arene, halogen, hydroxyl, carboxyl, and amine. $R^3$ preferably comprise a group selected from a phenyl group, an alkyl of 1-8 or a benzyl group.

In one embodiment Formula IV is an alkynyl sulfide. Alkynyl sulfides are accessible by direct deprotonation of terminal alkynes. The deprotonation is followed by interception with elemental sulfur followed by quenching the incipient sulfide anion with an aliphatic halide. In an alternate embodiment deprotonation is followed by direct reaction of the lithium acetylide intermediate with an appropriate dialkyl disulfide.

In an embodiment of the invention dimers or oligomers may be formed, preferably, at $R^1$, $R^2$, $R^3$ or $R^4$ as illustrated in FIG. 1B as exemplified by compounds 27 and 28 with the understanding that any of $R^1$, $R^2$, $R^3$ or $R^4$ could be substituted with Z. In compounds 27 and 28 $R^1$, $R^2$, $R^3$, X and n are defined elsewhere herein. In compounds 27 and 28 Z is a linking group and preferably an aliphatic, oligomeric glycol, or arene linking group with alkyl of 1 to 10 carbons being a preferred linking group. Compounds 27 and 28 are exemplary of similar linked compounds based on Formula I.

The solvent is not particularly limited, however, tetrahydrofuran (THF), acetonitrile (ACN), dichloromethane (DCM), toluene, lower alkyl alcohols such as methanol and ethanol, dialkyl ethers such as diethyl ether and chloroform have been demonstrated to be suitable for demonstration of the invention.

Throughout the specification the term aliphatic refers to a moiety of an alkyl, alkenyl or alkynyl and is intended to refer to a substituted or unsubstituted group which may be linear, branched or cyclic including those cyclic rings comprising a heteroatom as a substitute for a carbon in the ring unless otherwise specified.

Throughout the specification the term arene is intended to refer to a hydrocarbon arene moiety, also referred to in the art as an aryl, or a moiety of a heteroatom arene either of which may be substituted or unsubstituted. Included are fused arene groups unless otherwise specified. Particularly preferred arenes are aryls, oxygen containing arenes, nitrogen containing arenes and the like.

A drug substance is a molecular entity or compound, also known as an active pharmaceutical ingredient (API), or active pharmaceutical compound, that exhibits biological activity for the purpose of providing human or animal medication to treat disease, pain or any medically diagnosed condition. It is possible for a drug substance to be used in combination with one or more different drug substances to ultimately impart a biological response in humans or animals. For the purposes of this invention the drug substance is represented by Formula I. A drug substance is typically formulated into a drug product with other, non-biologically active compounds to provide a means of predictable and quantitative dosage delivery, or optionally to impart acceptable stability features to the drug product. In some embodiments additional biologically active compounds may be incorporated into a drug product to provide synergistic, complimentary or additional treatments.

A drug product is a formulation, mixture or admixture of the drug substance with combinations of excipients, processing aids, buffers and optionally other inert ingredients that allow delivery of the drug substance by the selected delivery mechanism to the patient at a predictable dosage. For the purposes of this invention a drug product comprises a drug substance represented by Formula I. Those elements of the drug product exclusive of the drug substance of interest are referred to as the carrier matrix without regard for the function of the components of the carrier matrix. Various delivery mechanisms include solid oral dosage, for example, pills, tablets, or capsules. Additional delivery systems can include solution or suspension injection dosage forms including depo drug products, transdermal patches, and nasal or inhalation devices. The dosage is the actual concentration delivered to the patient and is dependent upon many factors including the actual delivery system selected and the time between doses. The dosage may be available for essentially immediate release, release over time, or manipulated by additional means for stimulated release such as for example, by irradiation. The carrier matrix is composed of ingredients, or excipients, optionally selected from the group, but not limited to binders, fillers, flow enhancers, surfactants, disintegrants, buffers, and the like, typically employed in the art and found in the "Handbook of Pharmaceutical Excipients", Rowe, Sheskey and Owen (Editors), Fifth Edition, 2006, Pharmaceutical Press (publishers).

Throughout the description a range of subscripts, such as 1-10, is intended to be inclusive of all intervening integers. For example, 1-5 represents 1, 2, 3, 4 or 5 or any range there between such as 2-4.

EXAMPLES

Experimental Details

All reagents were purchased from commercial sources and used without purification. THF and acetonitrile were dried prior to use over sodium/benzophenone and phosphorous pentoxide, respectively. $^1H$ and $^{13}C$ nuclear magnetic resonance (NMR) spectra were collected on Bruker Avance 300 MHz, 500 MHz and JOEL Eclipse 500 MHz NMR spectrometers using $CDCl_3$. Chemical shifts are reported in parts per million (ppm). Spectra are referenced to residual solvent peaks. Infrared spectroscopy data were collected using a Shimadzu IRAffinity-1S instrument (with MIRacle 10 single reflection ATR accessory) operating over the range of 400 to 4000 $cm^{-1}$. Flash silica gel (40-63 µm) was used for column chromatography. All known compounds were characterized by $^1H$ and $^{13}C$ NMR and are in complete agreement with samples reported elsewhere. All new compounds were characterized by $^1H$ and $^{13}C$ NMR, attenuated total reflectance Fourier transform infrared (ATR-FTIR), high resolution mass spectroscopy (HRMS), x-ray diffraction (XRD), and melting point (where appropriate).

Synthesis of Alkynyl Sulfides

In one method the alkynyl sulfide was prepared by adding a solution of the terminal alkyne (1 equiv) in THF (5 mL for 1 mmol of alkyne) under argon atmosphere to a flame dried 2-neck round bottom flask following by addition of a solution of the terminal alkyne (1 equiv) in THF (5 mL for 1 mmol of alkyne) under argon atmosphere with stirring. A septum was placed over the round bottom inlets and the solution was cooled to about −78° C. A solution of n-BuLi (1.1 equiv, 1.6 M in hexane) was added. The reaction solution was stirred for 30 minutes followed by the addition of 1 molar equivalent of finely ground sulfur powder by briefly removing one of the septa and then replacing it. The resulting mixture was stirred for 1 hour at about −78° C. The resulting mixture was allowed to gradually warm to 0° C. until the sulfur was completely consumed, thus producing red colored lithium alkynyl thiolate. The corresponding alkyl halide (5.0 mmol, 1 equiv) was then added in a dropwise fashion. After 4 h the reaction mixture was quenched with saturated aqueous NH$_4$Cl (5 mL for 1 mmol of alkyne). The reaction mixture was then poured into a separatory funnel, and the aqueous layer was extracted with diethyl ether (3×5 mL for 1 mmol of alkyne). The combined ether extracts were washed with saturated aqueous brine (5 mL for 1 mmol of alkyne). The organic layer was then dried over Na$_2$SO$_4$, decanted, and the solvent was evaporated by rotary evaporation. The crude residue was then purified by flash chromatography (silica gel, hexane) to afford the desired alkynyl sulfide. The alkynyl sulfide used for the synthesis of Compounds 3-7 were synthesized using this protocol.

In a second method alkynyl sulfides were prepared by adding a solution of the terminal alkyne (1 equiv) dissolved in THF (1 mL for 1 mmol of alkyne) to a flame dried round bottom flask, equipped with a magnetic stir bar and a septum. The solution was then cooled to −78° C. and n-BuLi (1.1 equiv, 1.6 M in hexane) was added dropwise. This solution was stirred for 10 min after which dimethyl disulfide (1.2 equiv) was added at −78° C. The solution was then allowed to warm to room temperature and stirred for 1 hour. The reaction mixture was quenched with saturated aqueous NH$_4$Cl (5 mL for 1 mmol of alkyne) and extracted with ethyl acetate (3×5 mL for 1 mmol of alkyne). The combined organic layers were dried over Na$_2$SO$_4$, decanted, and concentrated by rotary evaporation. The crude mixture was purified by flash chromatography (silica gel, hexanes) to yield the desired alkynyl sulfide.

The corresponding alkynyl selenide analogs for the synthesis of 1,2-diazacyclobutenes for compounds 17 and 18 were synthesized using similar conditions as above.

General Synthesis of Diazacyclobutenes

To a flame dried round bottom flask equipped with a stir bar was added a solution of 4-phenyl-1,2,4-triazoline-3,5-dione (PTAD) (1 equiv) in dry acetonitrile (5 mL for 1 mmol of PTAD). To this stirring solution was added dropwise a solution of alkynyl sulfide or alkynyl selenide (1.3 equiv) in dry acetonitrile (5 mL for 1.3 mmol of alkynyl substrate). Then the round bottom flask was attached to a water cooled condenser and the mixture was refluxed for 24 h. The resultant mixture was concentrated under reduced pressure and purified via flash chromatography with hexane and ethyl acetate (gradient from 100% hexane to 80:20 hexane/ethyl acetate) to afford the corresponding diazacyclobutene.

Example 1: Synthesis of Compound 1

The yield for the formation of Compound 1 in a series of common solvents was determined by reacting PTAD (1 equiv.) and C$_6$H$_5$—CC—SCH$_3$ (1.3 equiv) in a series of common solvents. The mixtures were heated under reflux conditions for 24 hours. The results are reported in Table 1. Acetonitrile was found to afford the highest yield of 89% yield as indicated for Sample 5 even though the reaction tolerates a range of solvents reasonably well. Chloroform and dichloromethane resulted in slightly lower yields of 82% and 78%, respectively, whereas tetrahydrofuran and toluene provided even lower yields of 68% and 67% as evidenced by samples 1-4. Reaction conditions were further studied by conducting a time study by refluxing in acetonitrile for 6 hours (80%) and 12 hours (83%) resulting in good but slightly lower yields compared to the corresponding 24 hour reaction as evidenced by Samples 6-7. Furthermore, decreasing the equivalence of the alkynyl sulfide of Formula III resulted in lower isolated yields of product resulting in yields of 71%, 69%, and 72% for 1.0, 1.1, and 1.2 equiv of Formula III respectively, as evidenced in Samples 8-10. When the concentration of the reaction was doubled (i.e. to 0.2 M in PTAD), the yield was also diminished to 75%. Based on these observations the conditions used for Sample 5 were used for subsequent experiments. The cyclization of related N-methyl-N-tosyl ynamines and silyl ynol ethers proceeded rather poorly under the present reaction conditions (i.e. 30-40% yield) for ynamines in the presence of a Lewis acid catalyst.

TABLE 1

| Sample | Solvent | Molar Equivalents | time (H) | Yield (%) |
|---|---|---|---|---|
| 1 | CHCl$_3$ | 1.3 | 24 | 82 |
| 2 | DCM | 1.3 | 24 | 78 |
| 3 | THF | 1.3 | 24 | 68 |
| 4 | Toluene | 1.3 | 24 | 67 |
| 5 | ACN | 1.3 | 24 | 89 |
| 6 | ACN | 1.3 | 6 | 80 |
| 7 | ACN | 1.3 | 12 | 83 |
| 8 | ACN | 1.0 | 24 | 71 |
| 9 | ACN | 1.1 | 24 | 69 |
| 10 | ACN | 1.2 | 24 | 72 |
| 11 | ACN | 1.3 | 24 | 75 |

In Table 1 Molar Equivalents is the moles of Formula III per mole of Formula II, DCM is dichloromethane, THF is tetrahydrofuran, ACN is acetonitrile, yield is based on isolated material after column chromatography.

Example 2: Synthesis of Compounds 1-22

A series of diazacyclobutenes were prepared using PTAD as the reactant of Formula II wherein R$^2$ is phenyl. Varying the length of the alkyl chain resident on the sulfur atom, R$^2$, of the alkynyl sulfide component were prepared as Compounds 1-6. Products bearing shorter n-alkyl chains at R$^2$ such as methyl, ethyl, n-propyl, and n-butyl were successfully converted into their corresponding diazacyclobutene derivatives, Compounds 1-4, in 77-89% yields. The diazacyclobutene derivatives bearing n-pentyl and n-octyl groups at sulfur, Compounds 5 and 6, were generated in 78% and 81% yields, respectively. Incorporating a benzyl group at R$^2$, Compound 7, resulted in a moderate yield of 62%. The R$^3$=Ph analog, Compound 8, was prepared in 85% isolated yield at 1 mmol scale. The results are provided in Table 2:

TABLE 2

| Compound | R$^1$ | X | R$^3$ | Yield(%) |
|---|---|---|---|---|
| 1 | —C$_6$H$_5$ | S | —CH$_3$ | 89 |
| 2 | —C$_6$H$_5$ | S | —CH$_2$CH$_3$ | 84 |
| 3 | —C$_6$H$_5$ | S | —(CH$_2$)$_2$CH$_3$ | 80 |
| 4 | —C$_6$H$_5$ | S | —(CH$_2$)$_3$CH$_3$ | 77 |
| 5 | —C$_6$H$_5$ | S | —(CH$_2$)$_4$CH$_3$ | 78 |
| 6 | —C$_6$H$_5$ | S | —(CH$_2$)$_7$CH$_3$ | 81 |
| 7 | —C$_6$H$_5$ | S | —(CH$_2$)C$_6$H$_5$ | 62 |
| 8 | —C$_6$H$_5$ | S | —C$_6$H$_5$ | 81 |
| 9 | —C$_6$H$_4$CH$_3$ | S | —CH$_3$ | 92 |
| 10 | —C$_6$H$_4$CH$_3$ | S | —CH$_2$CH$_3$ | 77 |
| 11 | —C$_6$H$_4$OCH$_3$ | S | —CH$_3$ | 74 |
| 12 | —C$_6$H$_4$Cl | S | —CH$_3$ | 85 |
| 13 | —C$_6$H$_4$CF$_3$ | S | —CH$_3$ | 83 |
| 14 | —(CH2)$_3$CH$_3$ | S | —CH$_3$ | 61 |

TABLE 2-continued

| Compound | R$^1$ | X | R$^3$ | Yield(%) |
|---|---|---|---|---|
| 15 | —(CH2)$_3$CH$_3$ | S | —(CH$_2$)$_3$CH$_3$ | 56 |
| 16 | cyclopropyl | S | —CH$_3$ | 94 |
| 17 | —C$_6$H$_5$ | Se | —CH$_3$ | 80 |
| 18 | —C$_6$H$_5$ | Se | —C$_6$H$_5$ | 93 |
| 19 | —C$_6$H$_4$CF$_3$ | S | —(CH$_2$)$_2$C$_6$H$_5$ | 68 |
| 20 | —C$_6$H$_4$OCH$_3$ | S | —(CH$_2$)$_2$C$_6$H$_5$ | 89 |
| 21 | —C$_6$H$_5$ | N | —CH$_3$ and Ts | 27 |
| 22 | —C$_6$H$_4$CF$_3$ | N | —CH$_3$ and Ts | 40 | wherein Ts is tosylate.

Example 2: Synthesis of Compounds 23-25

A series of diazacyclobutenes were prepared using PTAD as the reactant of Formula II wherein R1, R$^2$ and R$^3$ are is indicated in Table 3:

TABLE 3

| Compound | R$^1$ | R$^2$ | X | R$^3$ | Yield(%) |
|---|---|---|---|---|---|
| 23 | —C$_6$H$_5$ | -m-C$_6$H$_4$Cl | S | —CH$_3$ | 30 |
| 24 | —C$_6$H$_5$ | -m-C$_6$H$_4$Cl | S | —CH$_2$CH$_3$ | 29 |
| 25 | —C$_6$H$_5$ | -m-C$_6$H$_4$OCH$_3$ | S | —CH$_3$ | 30 |

The reactivity of alkyl phenylacetylene sulfides bearing para-substituted electron donating and withdrawing substituents on the phenyl group situated at R$^1$ was evaluated. Substrates with arenes bearing electron donating groups such as p-methyl, represented by Compounds 9 and 10, and p-methoxy, represented by Compound 11, proceeded with good yield. Substrates with arenes bearing electron withdrawing substituents such as p-chloro, Compound 12, and p-trifluoromethyl, Compound 13, also generated the corresponding diazacyclobutene derivatives in good yields. Thioacetylenes bearing an alkyl chain at R$^1$ in lieu of an arene were evaluated. Compounds 14 and 15 were prepared in moderate yields of 61% and 56%, respectively. Additionally, Compound 16, where R$^1$=cyclopropyl, was prepared in 94% yield. The use of selenium as the chalcogen, as opposed to sulfur, provided 80 and 93% yield, as indicated for Compounds 17 and 18, respectively. The reaction also scales reasonably well. The synthesis of Compound 8 was carried out on a 6 mmol scale, returning the diazacyclobutene in 81% isolated yield (1.87 g).

Characterization of Various Compounds

Compound 1: Light yellow solid; Yield: 89% (288 mg); Mp: 98.6-99.6° C.; IR (neat): 2927 (w), 1784 (m), 1732 (s), 1595 (w), 1384 (s), 1220 (s), 696 (s), 686 (s) cm$^{-1}$; $^1$H-NMR (500 MHz, CDCl$_3$) δ 8.00-7.78 (m, 2H), 7.67-7.31 (m, 8H), 2.59 (s, 3H); $^{13}$C NMR (125 MHz, CDCl$_3$)δ=156.5, 155.1, 145.3, 130.8, 129.9, 129.3, 129.1, 128.8, 126.3, 125.6, 125.4, 17.4; HRMS (ESI$^+$): Calcd for C$_{17}$H$_{14}$N$_3$O$_2$S, [M+H]$^+$324.0807 Found m/z 324.0822.

Compound 2: Light yellow solid; Yield: 84% (283 mg); Mp: 90.6-91.2° C.; IR (neat): 3061 (w),2962 (w), 2929 (w), 1793 (m), 1726 (s), 1595 (w), 1386 (s), 1213 (s), 698 (s), 686 (s) cm$^{-1}$; $^1$H-NMR (500 MHz, CDCl$_3$) δ 7.92 (d, J=8.2 Hz, 2H), 7.78-7.29 (m, 8H), 3.06 (q, J=7.2 Hz, 2H), 1.41 (t, J=7.3 Hz, 3H); $^{13}$C NMR (125 MHz, CDCl$_3$) δ=156.3, 155.0, 146.9, 130.8, 129.9, 129.3, 129.1, 128.7, 128.1, 126.3, 125.5, 125.4, 29.2, 15.1; HRMS (ESI$^+$): Calcd for C$_{18}$H$_{16}$N$_3$O$_2$S, [M+H]$^+$ 338.0963 Found m/z 338.0980.

Compound 3: Light yellow solid; Yield: 80% (281 mg); Mp: 85.2-86.2° C.; IR (neat): 3068 (w), 2962 (w), 2929 (w), 2870 (w), 1793 (m), 1728 (s), 1593 (w), 1386 (s), 1213 (s), 700 (s), 686 (s) cm$^{-1}$; $^1$H-NMR (500 MHz, CDCl$_3$) δ 8.02-7.80 (m, 2H), 7.64-7.32 (m, 8H), 3.02 (t, J=6.4 Hz, 2H), 1.77 (q, J=7.3 Hz, 2H), 1.05 (t, J=7.3 Hz, 3H); $^{13}$C NMR (125 MHz, CDCl$_3$)δ=156.4, 155.1, 146.5, 130.9, 129.9, 129.3, 129.1, 128.7, 128.5, 126.4, 125.5, 125.4, 36.8, 23.2, 13.0; HRMS (ESI$^+$): Calcd for C$_{19}$H$_{18}$N$_3$O$_2$S, [M+H]$^+$ 352.1120 Found m/z 352.1129.

Compound 4: Light yellow solid; Yield: 77% (281 mg); Mp: 60.5-61.7° C.; IR (neat): 3066 (w),2960 (w), 2931 (w), 2872 (w), 2856 (w), 1788 (m), 1728 (s), 1595 (w), 1388 (s), 1217 (s), 698 (s), 684 (s) cm$^{-1}$; $^1$H-NMR (500 MHz, CDCl$_3$) δ 7.88 (d, J=7.5 Hz, 2H) 7.60-7.30 (m, 8H), 3.04 (t, J=7.5 Hz, 2H), 1.72 (p, J=7.3 Hz, 2H), 1.47 (sext, J=7.3 Hz, 2H), 0.92 (t, J=7.3 Hz, 3H); $^{13}$C NMR (125 MHz, CDCl$_3$) δ=156.4, 155.2, 146.5, 130.9, 129.9, 129.3, 129.1, 128.8, 128.6, 126.4, 125.5, 125.4, 34.6, 31.8, 21.5, 13.5; HRMS (ESI$^+$): Calcd for C$_{20}$H$_{20}$N$_3$O$_2$S, [M+H]$^+$ 366.1276 Found m/z 366.1286.

Compound 5: Light yellow solid; Yield: 78% (296 mg); Mp: 70.7-71.2° C.; IR(neat): 3066 (w), 2953 (w), 2927 (w), 2856 (w), 1791 (m), 1730 (s), 1595 (w), 1388 (s), 1213 (s), 698 (s), 684 (s) cm$^{-1}$; $^1$H-NMR (500 MHz, CDCl$_3$) δ 7.95-7.85 (m, 2H), 7.6-7.3 (m, 8H), 3.03 (t, J=7.3 Hz, 2H), 1.73 (p, J=7.3 Hz, 2H), 1.5-1.2 (m, 4H), 0.87 (t, J=7.1 Hz, 3H); $^{13}$C NMR (125 MHz, CDCl$_3$)δ=156.3, 155.2, 146.5, 130.9, 129.9, 129.3, 129.1, 128.7, 128.6, 126.4, 125.5, 125.4, 34.9, 30.5, 29.4, 22.1, 13.9; HRMS (ESI$^+$): Calcd for C$_{21}$H$_{22}$N$_3$O$_2$S, [M+H]$^+$ 380.1433 Found m/z 380.1437.

Compound 6: Light yellow solid; Yield: 81% (341 mg); Mp: 36.3-37.3° C.; IR (neat): 3066 (w), 2924 (m), 2852 (w), 1789 (m), 1732 (s), 1595 (w), 1386 (s), 1215 (s), 700 (s), 686 (s) cm$^{-1}$;$^1$H-NMR (300 MHz, CDCl$_3$) δ 7.89 (d, J=6.6 Hz, 2H), 7.6-7.3 (m, 8H), 3.03 (t, J=7.3 Hz, 2H), 1.73 (p, J=7.4 Hz, 2H), 1.56-1.36 (m, 2H), 1.35-1.15 (broad m, 8H), 0.86 (t, J=6.7 Hz, 3H); $^{13}$C NMR (75 MHz, CDCl$_3$)δ=156.4, 155.2, 146.5, 130.9, 129.9, 129.3, 129.1, 128.7, 128.6, 126.4, 125.5, 125.4, 34.9, 31.7, 29.8, 29.1, 29.0, 28.4, 22.6, 14.0; HRMS (ESI$^+$): Calcd for C$_{24}$H$_{28}$N$_3$O$_2$S, [M+H]$^+$ 422.1940 Found m/z 422.1909.

Compound 7: Light Pink solid; Yield: 62% (248 mg); Mp: 92.6-93.8° C.; IR (neat): 3061 (w), 3026 (w), 2929 (w), 2850 (w), 1786 (m), 1735 (s), 1595 (w), 1386 (s), 1224 (s), 694 (s), 682 (s) cm$^{-1}$; $^1$H-NMR (300 MHz, CDCl$_3$) δ 7.8-7.1 (m, 15H), 4.21 (s, 2H); $^{13}$C NMR (75 MHz, CDCl$_3$)δ=156.7, 154.9, 148.6, 136.3, 130.8, 130.1, 129.4, 129.2, 129.1, 128.6, 128.5, 127.8, 127.0, 125.9, 125.5, 125.5, 39.2; HRMS (ESI$^+$): Calcd for C$_{23}$H$_{18}$N$_3$O$_2$S, [M+H]$^+$ 400.1120 Found m/z 400.1136.

Compound 8: White Solid; Yield: 85% (328 mg); Mp: 171.7-172.7° C.;IR (neat): 2924 (w), 2850 (w), 1789 (m), 1732 (s), 1593 (w), 1577 (w), 1384 (s), 1215 (s), 1149 (s), 1006 (m), 918 (m), 740 (s) 682 (s) cm$^{-1}$;$^1$H-NMR (300 MHz, CDCl$_3$) δ 7.90-7.80 (m, 2H), 7.60-7.40 (m, 10H), 7.40-7.29 (m, 3H); $^{13}$C NMR (75 MHz, CDCl$_3$) δ=155.6, 154.8, 148.2, 131.8, 130.7, 130.6, 129.7, 129.6, 129.3, 129.1, 128.8, 128.1, 125.9, 125.9, 125.8, 125.4; HRMS (ESI$^+$): Calcd for C$_{22}$H$_{16}$N$_3$O$_2$S, [M+H]$^+$ 386.0963 Found m/z 386.0978.

Compound 9: White yellow solid; Yield: 92% (310 mg); Mp: 144.7-145.8° C.; IR (neat): 3072 (w), 3034 (w), 2997 (w), 2926 (w), 2850 (s), 1782 (m), 1724 (s), 1595 (w), 1382 (s), 1217 (s), 690 (s)cm$^{-1}$; $^1$H-NMR (300 MHz, CDCl$_3$) δ

7.78 (d, J=8.0 Hz, 2H), 7.6-7.4 (m, 5H), 7.27 (d, J=8.0 Hz, 2H), 2.58 (s, 3H), 2.41 (s, 3H); $^{13}$C NMR (75 MHz, CDCl$_3$)δ=156.7, 155.1, 145.9, 140.4, 130.9, 129.5, 129.3, 129.1, 128.3, 125.6, 125.4, 123.5, 21.6, 17.5; HRMS (ESI$^+$): Calcd for C$_{18}$H$_{16}$N$_3$O$_2$S, [M+H]$^+$ 338.0963 Found m/z 338.0978.

Compound 10: White solid; Yield: 77% (271 mg); Mp: 105.3-106.3° C.; IR (neat): 2966 (w), 2931 (w), 2866 (w), 1782 (m), 1728 (s), 1627 (w), 1597 (w), 1496 (m), 1388 (s), 1226 (s), 1145 (s), 1103 (s), 1018 (m), 921 (m), 875 (m), 813 (m), 767 (s), 686 (s) cm$^{-1}$; $^1$H-NMR (300 MHz, CDCl$_3$) δ 7.80 (d, J=8.2 Hz, 2H), 7.55-7.37 (m, 5H), 7.26 (d, J=8.01 Hz, 2H), 3.03 (q, J=7.3 Hz, 2H), 2.39 (s, 3H), 1.39 (t, J=7.3 Hz, 3H); $^{13}$C NMR (75 MHz, CDCl$_3$)δ=156.6, 155.1, 147.5, 140.5, 130.8, 129.4, 129.3, 129.1, 127.1, 125.6, 125.4, 123.5, 29.3, 21.6, 15.1; HRMS (ESI$^+$): Calcd for C$_{19}$H$_{18}$N$_3$O$_2$S, [M+H]$^+$352.1120 Found m/z 352.1130.

Compound 11: White solid; Yield: 74% (262 mg); Mp: 116.1-116.5° C.; IR (neat): 3070 (w), 3014 (w), 2962 (w), 2927 (w), 2837 (w), 1782 (m), 1724 (s), 1602 (m), 1384 (s), 1257 (s), 1226 (m), 688 (s)cm$^{-1}$;$^1$H-NMR (500 MHz, CDCl$_3$) δ 7.94-7.71 (m, 2H), 7.59-7.34 (m, 5H), 7.02-6.90 (m, 2H), 3.84 (s, 3H), 2.54 (s, 3H); $^{13}$C NMR (125 MHz, CDCl$_3$)δ=160.9, 156.9, 155.2, 145.9, 130.8, 129.2, 129.0, 127.4, 126.9, 125.3, 118.8, 114.2, 55.3, 17.6; HRMS (ESI$^+$): Calcd for C$_{18}$H$_{15}$N$_3$O$_3$S, [M+H]$^+$ 354.0912 Found m/z 354.0928.

Compound 12: White solid; Yield: 85% (304 mg); Mp: 135.8-136.9° C.; IR (neat): 3091 (w), 3072 (w), 2926 (w), 1784 (m), 1732 (s), 1593 (w), 1381 (s), 825 (s), 686 (s)cm$^{-1}$;$^1$H-NMR (500 MHz, CDCl$_3$) δ 7.80 (d, J=8.7 Hz, 2H), 7.58-7.36 (m, 7H), 2.59 (s, 3H); $^{13}$C NMR (125 MHz, CDCl$_3$)δ=156.2, 155.0, 144.0, 135.8, 130.7, 129.8, 129.4, 129.2, 129.1, 126.8, 125.4, 124.8, 17.3; HRMS (ESI$^+$): Calcd for C$_{17}$H$_{13}$N$_3$O$_2$SCl, [M+H]$^+$ 358.0417 Found m/z 358.0432.

Compound 13: White solid; Yield: 83% (325 mg); Mp: 79.6-81.4° C.; IR (neat): 3068 (w), 3045 (w), 2922 (w), 1788 (m), 1732 (s), 1614 (w), 1388 (s), 1317 (s), 696 (s), 684 (s)cm$^{-1}$; $^1$H-NMR (300 MHz, CDCl$_3$) δ 7.94 (d, J=8.2 Hz, 2H), 7.70 (d, J=8.2 Hz, 2H), 7.60-7.40 (m, 5H), 2.63 (s, 3H); $^{13}$C NMR (75 MHz, CDCl$_3$)δ=155.8, 155.0, 142.8, 131.8, 131.1 (q, $^2J_{c-F}$=32.9 Hz), 130.7, 129.7 (q, $^4J_{c-F}$=1.47 Hz), 129.4, 129.3, 125.8 (q, $^3J_{c-F}$=3.8 Hz), 125.6, 125.4, 123.7 (q, $^1J_{c-F}$=272.2 Hz), 17.1; HRMS (ESI$^+$): Calcd for C$_{18}$H$_{13}$N$_3$O$_2$SF$_3$, [M+H]$^+$ 392.0681 Found m/z 392.0693.

Compound 14: White solid; Yield: 61% (185 mg); Mp: 44.8-45.7° C.; IR (neat): 2958 (w), 2927 (w), 2860 (w), 1797 (m), 1739 (s), 1593 (w), 1390 (s), 1211 (m),694 (s) cm$^{-1}$; $^1$H-NMR (300 MHz, CDCl$_3$) δ 7.55-7.35 (m, 5H), 2.54 (t, J=7.5 Hz, 2H), 2.44 (s, 3H), 1.70 (p, J=7.5 Hz, 2H), 1.42 (sext, J=7.4 Hz, 2H), 0.95 (t, J=7.3 Hz, 3H); $^{13}$C NMR (75 MHz, CDCl$_3$)δ=156.7, 155.1, 150.5, 132.2, 130.9, 129.2, 128.9, 125.2, 28.0, 25.3, 22.1, 17.8, 13.4; HRMS (ESI$^+$): Calcd for C$_{15}$H$_{18}$N$_3$O$_2$S, [M+H]$^+$304.1120 Found m/z 304.1138.

Compound 15: Colorless liquid; Yield: 56% (193 mg); IR (neat): 2958 (w), 2931 (w), 2870 (w), 1793 (w), 1735 (s), 1597 (w), 1500 (m), 1458 (w), 1377 (s), 1211 (m), 1138 (m), 1072 (m), 999 (m), 921 (m), 748 (m), 690 (m) cm$^{-1}$; $^1$H-NMR (300 MHz, CDCl$_3$) δ 7.60-7.35 (m, 5H), 2.87 (bs, 2H), 2.54 (t, J=7.5 Hz, 2H), 1.80-1.55 (m, 4H), 1.52-1.35 (m, 4H), 1.00-0.85 (m, 6H); $^{13}$C NMR (75 MHz, CDCl$_3$) δ=156.5, 155.2, 151.7, 131.2, 130.9, 129.3, 128.9, 125.3, 34.2, 31.5, 28.1, 25.3, 22.1, 21.3, 13.5 (2C, See 2D-HMQC analysis); HRMS (ESI$^+$): Calcd for C$_{18}$H$_{24}$N$_3$O$_2$S, [M+H]$^+$ 346.1589 Found m/z 346.1608.

Compound 16: White solid; Yield: 94% (270 mg); Mp: 71.5-72.5° C.; IR (neat): 2924 (w), 1793 (w), 1739 (s), 1643 (w), 1593 (w), 1492 (m), 1454 (w), 1427 (w), 1388 (s), 1261 (m), 1215 (s), 1149 (s), 1091 (m), 999 (m), 972 (m), 775 (m), 756 (m), 690 (m) cm$^{-1}$; $^1$H-NMR (300 MHz, CDCl$_3$) δ 7.55-7.35 (m, 5H), 2.41 (s, 3H), 1.90-1.60 (m, 1H), 1.40-1.06 (bm, 2H), 1.06-0.90 (bm, 2H); $^{13}$C NMR (75 MHz, CDCl$_3$)δ=156.5, 154.9, 151.2, 130.7, 130.5, 129.1, 128.8, 125.1, 17.8, 6.9, 6.6.

Compound 17: White yellow solid; Yield: 80% (296 mg); Mp:82.6-83.9° C.; IR (neat): 3066 (w), 3016 (w), 2924 (w), 2850 (w), 1786 (m), 1732 (s), 1631 (w), 1597 (w), 1504 (m), 1489 (m), 1381 (s), 1222 (m), 1141 (s), 1095 (m), 1072 (m), 1018 (s), 758 (m), 744 (m), 682 (s) cm$^{-1}$; $^1$H-NMR (300 MHz, CDCl$_3$) δ 7.94-7.84 (m, 2H), 7.56-7.36 (m, 8H), 2.47 (s, 3H); $^{13}$C NMR (75 MHz, CDCl$_3$)δ=156.3, 154.9, 146.5, 130.8, 129.8, 129.3, 129.1, 128.7, 126.4, 125.3, 125.3, 121.3, 8.7; HRMS (ESI$^+$): Calcd for C$_{17}$H$_{14}$N$_3$O$_2$Se, [M+H]$^+$ 372.0251 Found m/z 372.0269.

Compound 18: White yellow solid; Yield: 93% (402 mg); Mp: 162-162.8° C.; IR (neat): 3070 (w), 2924 (w), 2850 (w), 1793 (m), 1735 (m), 1631 (w), 1593 (w), 1573 (w), 1384 (s), 1276 (m), 1215 (m), 1141 (m), 1107 (m), 1068 (m), 995 (m), 918 (m),883 (m), 756 (m), 736 (s), 686 (s) cm$^{-1}$; $^1$H-NMR (300 MHz, CDCl$_3$) δ 8.00-7.90 (m, 2H), 7.70-7.60 (m, 2H), 7.53-7.38 (m, 8H), 7.38-7.29 (m, 3H); $^{13}$C NMR (75 MHz, CDCl$_3$) δ=155.7, 154.8, 148.1, 132.2, 130.8, 130.4, 129.8, 129.3, 129.1, 128.8, 128.4, 128.2, 126.1, 125.6, 125.4, 120.7; HRMS (ESI$^+$): Calcd for C$_{22}$H$_{16}$N$_3$O$_2$Se, [M+H]$^+$ 434.0408 Found m/z 434.0417.

Parasite Viability Assays

To determine the impact of diazacyclobutene derivatives on the growth of African trypanosomes (*Trypanosoma brucei brucei*) as a representative parasite, bloodstream form (BSF) parasites (cell line 90-13, a 427 strain at 1×10$^5$ cell/mL) were seeded into 384-well black plates in 40 μL HMI-9 supplemented with 10% fetal bovine serum and 10% Serum Plus (Sigma-Aldrich, St. Louis Mo.) in the presence of compound or equivalently diluted carrier. After 48 hours at 37° C. in 5% CO$_2$, CellTiter Blue (8 μL, Promega, Madison Wis.) was added and the plates incubated an additional 3 hours. Fluorescence emission at A$_{585}$ was then measured after excitation at A$_{546}$ on a Synergy H1 Hybrid Reader (Biotek, Winooski Vt.). Averages of triplicates were calculated and fit to dose-response curves using Prism (Graphpad, San Diego Calif.) for the determination of EC$_{50}$ values.

Various examples of Formula I were tested for viability with the results presented in Table 5;

TABLE 5

| Compound | EC50 (μM) | % BSF Growth Inhibition @ 10 μM |
| --- | --- | --- |
| 1 | >10 | 35.6 ± 1.9 |
| 2 | >10 | 23.4 ± 5.7 |
| 3 | 5.83 ± 2.2 | 96.6 ± 0.3 |
| 4 | >5 | 80.5 ± 2.1 |
| 5 | 2.65 ± 0.16 | 98.21 ± 0.17 |
| 6 | 2.04 ± 0.21 | 94.71 ± 3.48 |
| 7 | 0.386 ± 0.034 | 98.87 ± 2.68 |
| 8 | >10 | 11.5 ± 7 |
| 9 | >10 | |
| 10 | 3.66 ± 1.7 | 95.2 ± 3.5 |
| 11 | >5 | 77.1 ± 3.5 |
| 12 | >5 | 62.2 ± 2.7 |
| 13 | >2.5 | 89.6 ± 2.8 |
| 14 | 0.35 ± 0.04 | 95.6 ± 1.2 |

TABLE 5-continued

| Compound | EC50 (µM) | % BSF Growth Inhibition @ 10 µM |
|---|---|---|
| 15 | $10 > EC_{50} > 5$ | 59.2 ± 6.6 |
| 17 | >10 | 46.1 ± 6.2 |
| 18 | $10 > EC_{50} > 5$ | 84.24 ± 8.21 |
| 21 | >10 | 2.5 ± 4.3 |
| 22 | >10 | 0 |
| 23 | 7.08 ± 1.9 | |
| 24 | $10 > EC_{50} > 5$ | |
| 25 | >10 | |

In Table 5, $EC_{50}$ refers to the concentration of a drug, antibody or toxicant which induces a response halfway between the baseline and maximum after a specified exposure time.

Figure 2:
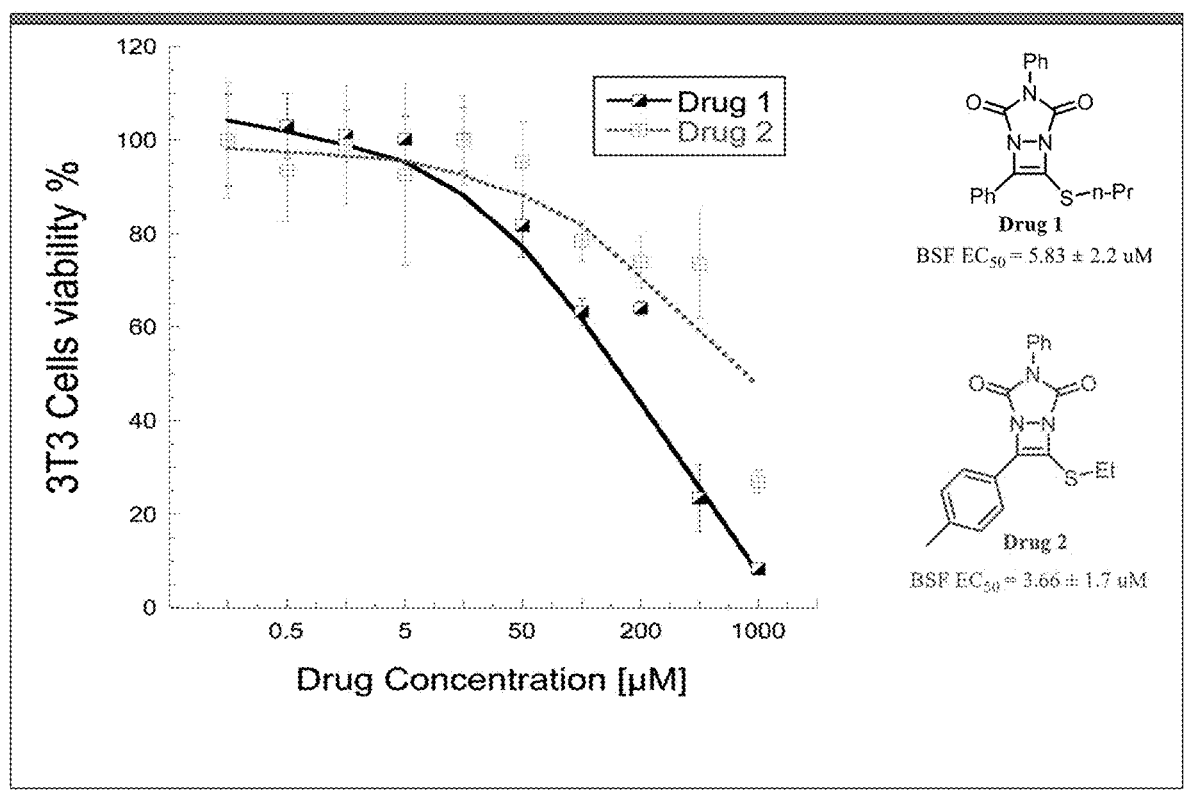
FIG. 2 is a graphical representation of a cytotoxicity study of an embodiment of the invention.

A cytotoxicity study was done with the results presented in FIG. 2. In FIG. 2, Drug 1 is Compound 3, Drug 2 is Compound 10 and 3T3 are 3-day transfer, inoculum $3 \times 10^5$ cells.

The invention has been described with reference to the preferred embodiments without limit thereto. One of skill in the art would realize additional embodiments and improvements which are not specifically stated but which are within the meets and bounds of the claims appended hereto.

The invention claimed is:

1. A drug product comprising:
a carrier matrix; and
a drug substance having the formula:

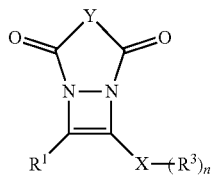

wherein:
$R^1$ is selected from the group consisting of H, aliphatic of 1 to 100 carbons and arene of up to 100 carbons and a linking group;
each $R^3$ is independently selected from the group consisting of H, aliphatic of 1 to 100 carbons and arene of up to 100 carbons;
Y is selected from the group consisting of $—(CR^4{}_A)_m—$, $—NR^2—$ and $—O—$;
wherein m is an integer selected from 1 and 2;
A is an integer of 1 or 2,
$R^2$ is selected from the group consisting of H, aliphatic, of 1 to 100 carbons and arene of up to 100 carbons; and
each $R^4$ is independently selected from the group consisting of H, aliphatic of 1 to 100 carbons and arene of up to 100 carbons and combinations thereof;
X is selected from the group consisting of B, O, N, S, Se and P; and
n is 1-4 as necessary to complete the valence of X.

2. The drug product of claim 1 wherein said $R^2$ is substituted.

3. The drug product of claim 2 wherein said $R^2$ is substituted with substituent selected from the group consisting of halogen, aliphatic, arene, hydroxyl, carboxyl, carbonate, ester, acetal, acid halide, thioester, aldehyde, ether, carbamate, amine, amide, nitro, imine, urea, oxime, hydrazine, azo, azide, isocyanate, ketene, nitrone, nitroso, nitrate ester, acyl, thiol, thioacetal, sulfide, disulfide, sulfoxide, sulfone, sulfonic acid, thiosulfonate, sulfonate ester, sulfate ester, thiocyanate, phosphine oxide, phosphite ester, phosphonate ester, phosphate ester, phosphate, phosphine, phosphite, borane, boric acid, boronic acid, borate ester, acyl halide, acyl anhydride, nitrile and an organometallic.

4. The drug product of claim 3 wherein said $R^2$ is substituted with a substituent selected from the group consisting of halogen, alkyl, aryl, hydroxyl, carboxyl and carbonate.

5. The drug product of claim 1 wherein each said $R^4$ is independently selected from the group consisting of H, aliphatic of 1 to 100 carbons and arene of up to 100 carbons and combinations thereof, the aliphatic or arene may be unsubstituted or substituted with a substituent selected from the group consisting of halogen, aliphatic, arene, hydroxyl, carboxyl, carbonate, ester, acetal, acid halide, thioester, aldehyde, ether, carbamate, amine, amide, nitro, imine, urea, oxime, hydrazine, azo, azide, isocyanate, ketene, nitrone, nitroso, nitrate ester, acyl, thiol, thioacetal, sulfide, disulfide, sulfoxide, sulfone, sulfonic acid, thiosulfonate, sulfonate ester, sulfate ester, thiocyanate, phosphine oxide, phosphite ester, phosphonate ester, phosphate ester, phosphate, phosphine, phosphite, borane, boric acid, boronic acid, borate ester, acyl halide, acyl anhydride, nitrile and an organometallic.

6. The drug product of claim 5 wherein each said $R^4$ is taken together to form an organic ring, a heteroatom ring or an arene.

7. The drug product of claim 6 wherein each said $R^4$ is taken together to form a phenyl ring.

8. The drug product of claim 1 wherein at least one of said $R^1$ or $R^3$ is substituted.

9. The drug product of claim 8 wherein at least one of said $R^1$ or $R^3$ is substituted with substituent selected from the group consisting of halogen, aliphatic, arene, hydroxyl, carboxyl, carbonate, ester, acetal, acid halide, thioester, aldehyde, ether, carbamate, amine, amide, nitro, imine, urea, oxime, hydrazine, azo, azide, isocyanate, ketene, nitrone, nitroso, nitrate ester, acyl, thiol, thioacetal, sulfide, disulfide, sulfoxide, sulfone, sulfonic acid, thiosulfonate, sulfonate ester, sulfate ester, thiocyanate, phosphine oxide, phosphite ester, phosphonate ester, phosphate ester, phosphate, phosphine, phosphite, borane, boric acid, boronic acid, borate ester, acyl halide, acyl anhydride, nitrile and an organometallic.

10. The drug product of claim 9 wherein at least one of said $R^1$ or $R^3$ is substituted with a substituent selected from the group consisting of halogen, alkyl, aryl, hydroxyl, carboxyl and carbonate.

11. The drug product of claim 1 wherein said X is selected from the group consisting of S, Se, N and O.

12. The drug product of claim 11 wherein said X is selected from the group consisting of S and Se.

13. The drug product of claim 1 wherein said n is 1 or 2.

14. The drug product of claim 1 wherein said drug substance has the formula:

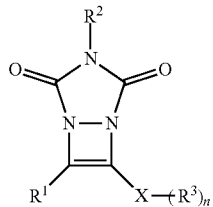

wherein:
R$^2$ is selected from the group consisting of H, aliphatic of 1 to 100 carbons and arene of up to 100 carbons.

15. The drug product of claim 14 wherein at least one of said R$^1$, R$^2$ or R$^3$ is substituted.

16. The drug product of claim 15 wherein at least one of said R$^1$, R$^2$ or R$^3$ is substituted with substituent selected from the group consisting of halogen, aliphatic, arene, hydroxyl, carboxyl, carbonate, ester, acetal, acid halide, thioester, aldehyde, ether, carbamate, amine, amide, nitro, imine, urea, oxime, hydrazine, azo, azide, isocyanate, ketene, nitrone, nitroso, nitrate ester, acyl, thiol, thioacetal, sulfide, disulfide, sulfoxide, sulfone, sulfonic acid, thiosulfonate, sulfonate ester, sulfate ester, thiocyanate, phosphine oxide, phosphite ester, phosphonate ester, phosphate ester, phosphate, phosphine, phosphite, borane, boric acid, boronic acid, borate ester, acyl halide, acyl anhydride, nitrile and an organometallic.

17. The drug product of claim 16 wherein at least one of said R$^1$, R$^2$ or R$^3$ is substituted with a substituent selected from the group consisting of halogen, alkyl, aryl, hydroxyl, carboxyl and carbonate.

18. The drug product of claim 14 wherein said X is selected from the group consisting of S, Se, N and O.

19. The drug product of claim 14 wherein said X is selected from the group consisting of S and Se.

20. The drug product of claim 14 wherein said n is 1 or 2.

21. The drug product of claim 1 wherein said carrier matrix comprises at least one material selected from the group consisting of binders, fillers, flow enhancers, surfactants, disintegrants and buffers.

* * * * *